(12) United States Patent
Araki et al.

(10) Patent No.: US 9,167,805 B2
(45) Date of Patent: Oct. 27, 2015

(54) METHOD OF ESTABLISHING MOUSE STRAIN

(75) Inventors: Masatake Araki, Kumamoto (JP); Kimi Araki, Kumamoto (JP)

(73) Assignee: National University Corporation Kumamoto University, Kumamoto (JP)

( * ) Notice: Subject to any disclaimer, the term of this patent is extended or adjusted under 35 U.S.C. 154(b) by 0 days.

(21) Appl. No.: 13/818,906

(22) PCT Filed: Aug. 30, 2011

(86) PCT No.: PCT/JP2011/069612
§ 371 (c)(1),
(2), (4) Date: Apr. 29, 2013

(87) PCT Pub. No.: WO2012/029784
PCT Pub. Date: Mar. 8, 2012

(65) Prior Publication Data
US 2013/0211187 A1 Aug. 15, 2013

(30) Foreign Application Priority Data
Aug. 31, 2010 (JP) ................................. 2010-194910

(51) Int. Cl.
*A01K 67/027* (2006.01)
*A61D 19/04* (2006.01)

(52) U.S. Cl.
CPC ............ *A01K 67/0271* (2013.01); *A61D 19/04* (2013.01); *A01K 2227/105* (2013.01)

(58) Field of Classification Search
CPC ..................... A01K 2227/105; A01K 2207/15; A01K 2207/12; A01K 2227/10
See application file for complete search history.

(56) References Cited

U.S. PATENT DOCUMENTS

| | | | |
|---|---|---|---|
| 2005/0125853 A1 | 6/2005 | Parekh | |
| 2006/0265774 A1 | 11/2006 | Shinohara et al. | |
| 2007/0250943 A1* | 10/2007 | Nagao et al. | 800/24 |

FOREIGN PATENT DOCUMENTS

| | | |
|---|---|---|
| JP | 2004-65040 | 3/2004 |
| WO | 2004/092357 | 10/2004 |
| WO | 2006/009297 | 1/2006 |

OTHER PUBLICATIONS

Carstea et al. "Germline competence of mouse ES and iPS cell lines: Chimera technologies and genetic background." World J Stem Cells (Dec. 31, 2009); 1(1):pp. 22-29.*
Tachibana et al. "Generation of Chimeric Rhesus Monkeys." Cell (Jan. 2012); 148(1): pp. 285-295.*
Takahashi et al. "Induction of Pluripotent Stem Cells from Mouse Embryonic and Adult Fibroblast Cultures by Defined Factors." Cell ( 2006); 126: pp. 663-676.*
Tanaka et al., Dullard is required for mouse primordial germ cell formation, Program Abstr Book Ann. Meet . Jpn Soc Dev Biol, 43:226 (Jul. 6, 2010).
International Search Report for International Application No. PCT/JP2011/069612 dated Dec. 6, 2011.

* cited by examiner

*Primary Examiner* — Thaian N Ton
*Assistant Examiner* — Titilayo Moloye
(74) *Attorney, Agent, or Firm* — Fish & Richardson P.C.

(57) ABSTRACT

A method of producing a chimera animal, characterized by transplanting, into a host animal, an aggregate of a first pluripotent stem cell that is of interest to strain establishment, a second pluripotent stem cell in which the ability to form germ cells is absent or decreased, and embryo.

4 Claims, No Drawings

METHOD OF ESTABLISHING MOUSE STRAIN

CROSS-REFERENCE TO RELATED APPLICATIONS

This is the U.S. National Phase, submitted pursuant to 35 U.S.C. §371, of International Patent Application No. PCT/2011/069612 filed on Aug. 30, 2011, which claims priority to application no. JP 2010-194910 filed in Japan on Aug. 31, 2010. The disclosures of these prior applications are hereby incorporated by reference and in their entireties.

TECHNICAL FIELD

The present invention relates to a method for efficiently establishing a mouse strain from a pluripotent stem cell.

BACKGROUND ART

In general, in order to produce a chimeric mouse from ES cells, two types of cells, namely, an ES cell of interest and a normal mouse embryo, can be mixed to allow ontogenesis. Furthermore, ES cells are used in an attempt to produce various chimeric animals (Patent Documents 1 and 2).

Depending on the properties of the ES cells, however, ontogenesis may not proceed normally in a chimeric embryo having a high rate (chimerism rate) of mixed ES cells, in which case the embryo may die before birth. On the other hand, there are also ES cells which may result in the birth of chimeras having a high chimerism rate but those chimeras have abnormal spermatogenetic ability and thus are unable to establish a mouse strain.

PRIOR ART DOCUMENTS

Patent Documents

[Patent Document 1] US Patent Application No. 2005/0125853 (specification)
[Patent Document 2] International Publication No. 2006/009297 (pamphlet)

SUMMARY OF THE INVENTION

Problem to be Solved by the Invention

The present invention has an objective of providing a method for efficiently establishing an animal strain such as a mouse strain from a pluripotent stem cell.

Means for Solving Problems

The present inventors have earnestly conducted a study on the above-described problems and, as a result of which, found that a mouse strain of interest can efficiently be established by mixing a pluripotent stem cell in which a gene of interest has been modified, together with a pluripotent stem cell associated with low or lack of spermatogenetic ability and an embryo, and transferring the mixed embryo into a surrogate mother, thereby accomplishing the present invention.

Hence, the present invention is a method for producing a chimeric animal, comprising a step of transferring an aggregate of a first pluripotent stem cell that is of interest to strain establishment, a second pluripotent stem cell associated with lack or low ability to form germ cells and an embryo into a host animal.

Examples of the pluripotent stem cell include an ES cell and an iPS cell. In one aspect of the present invention, the ability to form germ cells is, for example, spermatogenetic ability.

An example of the host animal subjected to transfer includes, but not limited to, a mouse.

According to the present invention, the second pluripotent stem cell may be a cell identified by accession number NITE BP-973, receipt number NITE ABP-1135 or receipt number NITE ABP-1136. In a preferable aspect, the second pluripotent stem cell has epigenetic property.

Furthermore, the present invention is a helper cell that is capable of enhancing the strain establishment efficiency of a pluripotent stem cell that is of interest to the strain establishment, wherein the helper cell is made of a pluripotent stem cell associated with lack or low ability to form germ cells. Examples of such helper cell include those identified by accession number NITE BP-973, receipt number NITE ABP-1135 and receipt number NITE ABP-1136.

Effect of the Invention

The present invention provides a method for efficiently establishing a mouse strain from a pluripotent stem cell. The method of the present invention is capable of efficiently acquiring a pup derived from an ES cell of interest with normal spermatogenetic ability.

EMBODIMENTS FOR CARRYING OUT THE INVENTION

Hereinafter, the present invention will be described in detail.

1. General Outline

The present invention is a method for producing a chimeric animal, comprising the step of transferring an aggregate of a first pluripotent stem cell that is of interest to strain establishment, a second pluripotent stem cell associated with lack or low ability to form germ cells (helper cell) and an embryo into a host animal, wherein the use of the helper cell allows efficient establishment of an animal strain from a pluripotent stem cell.

Although use of an ES cell alone often fails to give an animal (e.g., chimeric mouse) with a high chimerism rate, a chimeric animal can efficiently be established by mixing a pluripotent stem cell such as an ES cell or an iPS cell, an ES cell having no or low spermatogenetic ability (helper ES cell) and an embryo and transferring the resultant into a host animal.

The present invention is a method for producing a chimeric animal (e.g., a chimeric mouse), comprising the step of mixing three types of cells, namely, a pluripotent stem cell that is of interest to strain establishment, a helper cell and a normal embryo. Due to the contribution of the helper cell, ontogenesis proceeds normally and gives a chimeric embryo with a high chimerism rate. Then, this chimeric mouse (male) is mated with a normal female so that a pup derived from the ES cell of interest with normal spermatogenetic ability can be obtained, thereby establishing a mouse strain.

2. First Pluripotent Stem Cells

A first pluripotent stem cell used with the present invention is a cell that is injected into an embryo upon producing a chimeric animal and that is of interest to strain establishment.

The term "strain establishment" means that a cell is incorporated into a germline so that the character of the animal is passed on to the next generations.

The type of the first pluripotent stem cell is not particularly limited and examples include a normal embryonic stem cell (ES cell), an iPS cells, and a gene-modified cells.

TT2 cell, AB-1 cell, J1 cell, R1 cell or the like may appropriately be selected and used as the ES cell. In the present invention, cells obtained by making modification to these ES cells may also be used. Examples of such cell include cells obtained by modifying TT2 ES cells such that they can sustain without a feeder cell (KTPU10 ES cell, KTPU8 ES cell, etc.).

iPS cells are called artificial pluripotent stem cells or induced pluripotent stem cells, which are cells that have acquired pluripotency comparable to ES cells by introducing several types of transcription factor genes into somatic cells such as fibroblasts.

Mouse iPS cells are established by introducing four genes Oct3/4, Sox2, c-Myc and Klf4 into mouse fibroblasts (Takahashi K. et al., Cell 126:663-676, 2006), while human iPS cells have been established as well (Takahashi K. et al., Cell 131, 861-872, 2007).

A cell that has been genetically-engineered (targeted) such that a predetermined function of a gene of interest is reduced as compared to that of a wild-type cell or such that the gene of interest is knocked out, may also be used as a pluripotent stem cell of the present invention that is of interest to strain establishment. For modification of the gene of interest (gene targeting), general knockout technique, gene trapping or the like can be employed. Gene trapping is an approach which utilizes the fact that when a trap vector is introduced into a pluripotent stem cell, it is randomly integrated into an endogenous gene of an animal so that the trap vector is inserted into a specific gene on the genome to trap the specific gene (for example, see Araki K. et al., Cellular and Molecular Biology 45(5), 737-750, 1999).

3. Second Pluripotent Stem Cell

The second pluripotent stem cell is a pluripotent stem cell with no or lower reproduction competence as compared to that of a wild-type cell, and is mixed with the above-described first pluripotent stem cell to form an aggregate with an embryo. Although a chimeric animal that is highly efficient in strain establishment is difficult to obtain with the first pluripotent stem cell alone, the strain establishment efficiency of the first pluripotent stem cell can be enhanced by introducing the second pluripotent stem cell. Thus, the second pluripotent stem cell is called a "helper cell" (a "helper ES cell" when an ES cell is used).

The helper cell is not limited as long as it has no or low reproduction competence. According to the present invention, it is preferably one without spermatogenetic ability or one with low spermatogenetic ability. The type of the helper cell is, similar to the first pluripotent stem cell, a pluripotent stem cell such as an ES cell or an iPS cell.

As the helper ES cell, Ayu21-16 ES cell strain, Ayu21-16EG4 ES cell strain or CTB28 ES cell strain can be used. Ayu21-16 ES cell is one of trap clones obtained by introducing an exchangeable gene trap vector into KTPU10 ES cell resulting from modification of TT2 ES cell (Yagi T. et al., Anal. Biochem., 214, 70-76, 1993) that is generally used for production of a knockout mouse to sustain without a feeder cell, and traps a gene called heat shock protein 8 (Hspa8) present on mouse chromosome 9.

Ayu21-16 ES cell was designated "Ayu21-16" and internationally deposited with the Patent Microorganisms Depositary, National Institute of Technology and Evaluation (Patent Microorganisms Depositary, Biological Resource Center, NITE, 2-5-8, Kazusakamatari, Kisarazu-shi, Chiba, 292-0818, JAPAN) on Aug. 25, 2010 (date of receipt) under the Budapest Treaty. Its accession number is "NITE BP-973" (date of original deposit: Aug. 25, 2010).

Detailed information of Ayu21-16 ES cell is publicly available on database EGTC (see WorldWideWeb at egtc.ip) and is partially provided below.

<Ayu21-16>
DDBJ/GenBank/EMBL Accession Number; AB 187233
Gene Name; heat shock protein 8
Gene Symbol; Hspa8
Genomic Location; chr9: 40, 609, 200-40, 613, 500
Synonyms; Hspa10, Hsc73, Hsc70, Hsc71, 70 kDa, Hsp73
NCBI Gene ID; 15481
MGI ID; 105384
IGTC ID; 12489
KEGG Pathway; mmu03040 Splicesome
mmu04010 MAPK signaling pathway
mmu04144 Endocytosis
mmu04612 Antigen processing and presentation
CARD ID; 687

According to the present invention, a cell strain derived by introducing a reporter gene into Ayu21-16 ES cell strain described above or a cell strain derived by replacing the reporter gene contained in Ayu21-16 ES cell strain with other reporter gene can be used as a helper cell. For example, a cell strain (referred to as "Ayu21-16EG4 ES") in which reporter gene β-geo within the trap vector of Ayu21-16 ES cell strain has been replaced with different reporter gene, EGFP, can be used.

The gene to be introduced is not limited to the above-mentioned reporter genes and genes RFP, DsRed or the like may also be introduced. By doing so, the cell can be distinguished from other cells using fluorescence as an indicator.

Ayu21-16 EG4 ES cell was designated "Ayu21-16EG4" and internationally deposited with the Patent Microorganisms Depositary, National Institute of Technology and Evaluation (Patent Microorganisms Depositary, Biological Resource Center, NITE, 2-5-8, Kazusakamatari, Kisarazu-shi, Chiba, 292-0818, JAPAN) on Aug. 25, 2011 (date of receipt) under the Budapest Treaty. Its receipt number (indicated on the certificate of receipt) is "NITE ABP-1135".

CTB28 ES cell can be obtained by introducing a targeting vector, in order to knock out the predetermined gene, into KTPU8 ES cell resulting from modification of TT2 ES cell (Yagi T. et al., Anal. Biochem., 214, 70-76, 1993) to sustain without a feeder cell.

CTB28 ES cell was designated "CTB28" and internationally deposited with the Patent Microorganisms Depositary, National Institute of Technology and Evaluation (Patent Microorganisms Depositary, Biological Resource Center, NITE, 2-5-8, Kazusakamatari, Kisarazu-shi, Chiba, 292-0818, JAPAN) on Aug. 25, 2011 (date of receipt) under the Budapest Treaty. Its receipt number (indicated on the certificate of receipt) is "NITE ABP-1136".

The second pluripotent stem cell of the present invention, in particular a helper ES cell, is a helper cell with epigenetic property.

Here, "epigenetic" refers to modification that activates or inactivates gene expression without changing the nucleotide sequence of DNA, that is, a phenomenon that influences expression of a gene by a mechanism other than mutation of the genome itself. Examples of such modification include, in general, methylation of DNA, or acetylation, methylation or phosphorylation of histone. According to the present invention, the feature of the second pluripotent stem cell, namely, no or low ability to form germ cell, is attributed to its epigenetic property, which is not passed on to the following generations.

4. Production of Chimeric Animal

A chimeric animal can be produced by a standard method. The types of animal used in the present invention is a non-human mammal and not particularly limited. For example, a rodent such as a mouse, a rat, a guinea pig or a hamster, an experimental animal such as a rabbit, a dog, a cat or a monkey, or a livestock such as a sheep, a goat, a pig, a horse or a bovine can be used. According to the present invention, a mouse or a rat is favorable in terms of easy handling and high breeding ability.

Hereinafter, mice will be taken as an example for the sake of convenience.

A pluripotent stem cell (ES cell, iPS cell, etc.) that is of interest to strain establishment and a helper cell are introduced into an embryo. This transplanted embryo is transferred into the uterus of a pseudopregnant surrogate mother which will carry the embryo to term, thereby producing a chimeric mouse.

Here, "embryos" refer to individuals at stages from fertilization to birth during ontogenesis, and comprises 2-cell stage embryos, 4-cell stage embryos, 8-cell stage embryos, morula stage embryos, blastocysts and the like.

As a method for generating an aggregate by introducing pluripotent stem cells into an embryo, a known approach such as a microinjection technique or an aggregation technique can be used. An "aggregate" refers to an aggregate which is formed when the first and second pluripotent stem cells and the embryo are spatially present together, and may refer to either a form where the first and second pluripotent stem cells are injected into the embryo or a form where the embryo is separated into individual cells and aggregated with the first and second pluripotent stem cells.

A chimeric embryo is produced, first, by mating a female mouse which has been subjected to ovarian hyperstimulation with hormones with a male mouse. Then, early embryos are collected from the oviduct or the uterus 2.5 days after fertilization when an 8-cell stage embryo is used or 3.5 days after fertilization when a blastocyst is used, respectively. To the collected embryo, a first pluripotent stem cell (a cell that is of interest to strain establishment) and a second pluripotent stem cells (a helper cell) are injected to generate a chimeric embryo. The mix ratio of the first pluripotent stem cells and the second pluripotent stem cells is 1:9-9:1, and preferably 1:1.

When a microinjection technique is employed, the first and second pluripotent stem cells are injected into the collected embryo to generate a cell aggregate.

When an aggregation technique is employed, the first and second pluripotent stem cells may be mixed and sprinkled on a zona-free normal embryo for aggregation.

Meanwhile, a pseudopregnant female mouse to be a surrogate mother can be obtained by mating a female mouse undergoing normal oestrus cycle with a male mouse castrated by vasoligature or the like. A chimeric embryo generated according to the above-described method is transferred into the uterus of the prepared pseudopregnant mouse which will then carry the embryo to term, thereby producing a chimeric mouse.

Among such chimeric mice, a male mouse derived from embryos transplanted with the pluripotent stem cell are selected. Once the selected male chimeric mouse is mature, this mouse is mated with a pure strain female mouse. Incorporation of the pluripotent stem cell into the germline of the chimeric mouse can be confirmed as the fur color of the mouse derived from the first pluripotent stem cell appears on the pup.

Hereinafter, the present invention will be described more specifically by means of examples. The present invention, however, should not be limited to these examples.

Example 1

Ayu21-16 ES cell (NITE BP-973) has a high probability of resulting 100% chimeric mice (mice in which contribution rate of the ES cell is almost 100% as judged by the fur color) and results in a large number of chimeric mice to term. However, it is also characterized in that the failure of spermatogenesis due to, for example, atrophy of testes is seen in the resulting male chimeric mice by the time of mating (8 weeks or later following birth), which makes it difficult to give pups (F1). In accidentally acquired F1 mice, abnormal spermatogenesis was not observed and they were able to establish a mouse line without particular difficulty (already deposited with the CARD R-BASE).

Therefore, the failure of spermatogenesis observed in chimeric male mice does not seem to be caused by the influence of knocked out gene (Hspa8) but due to the property (epigenetic property) unique to this ES cell.

The reporter gene: β-geo within the trap vector of this Ayu21-16 ES cell was replaced with other reporter gene, i.e., gene EGFP, to give Ayu21-16EG4 ES cell strain (helper ES cell strain). The reporter gene was replaced according to publicly available method by taking advantage of the nature of the exchangeable gene trapping (for example, see Taniwaki T. et al., Dev. Growth Differ., 47, 163-172, 2005).

Since this ES cell and the differentiated cells thereof express reporter protein GFP (green fluorescence protein), they emit green fluorescence under UV ultraviolet light and thus they can easily be distinguished from other cells under a fluorescence microscope.

The ES cell strain that did not give a chimeric mouse with a high chimerism rate and thus failed to establish a strain by a usual method was mixed with Ayu21-16EG4 ES cell strain (helper ES cell) to produce a chimeric mouse. Furthermore, a male chimeric mouse was mated with a normal female mouse to see whether sperm derived from the ES cell of interest fertilized to deliver a pup, in other words, whether the ES cell of interest was incorporated into the germline in the chimeric mouse. The results are shown in Table 1.

The experiment was performed for 10 different ES cell stains, and F1 mice derived from the ES cell of interest were obtained for 6 strains (60%) (Table 1).

TABLE 1

| | | State of germline | |
|---|---|---|---|
| No. | Name of ES cells | Single line | Ayu21-16EG4-mixed line |
| 1 | Ayu21-W181 | x | x |
| 2 | Ayu21-W143 | x | o |
| 3 | Ayu21-B196 | x | o |
| 4 | Ayu21-T256 | x | x |
| 5 | Ayu21-W45 | x | x |
| 6 | mRBP4-19 | x | o |
| 7 | Girk2 CKO | x | x |

TABLE 1-continued

| | | State of germline | |
|---|---|---|---|
| No. | Name of ES cells | Single line | Ayu21-16EG4-mixed line |
| 8 | Ayu21-T191 | x | o |
| 9 | Ayu21-T346 | x | o |
| 10 | Ayu21-T343 | x | o |

Detailed experimental data of Ayu21-B196 will be described.

Ayu21-B196 ES cell is one of the trap clones obtained by introducing exchangeable gene trap vector pU-21B into KTPU8 ES cell, i.e., a feeder-free TT2 ES cell.

Ayu21-B196 ES cell traps a gene called adiponectin receptor 2 (Adipor2) present on mouse chromosome 6. Detailed information of Ayu21-B196 ES cell is publicly available on and is partially provided below.

<Ayu21-B196>
DDBJ/GenBank/EMBL Accession Number; AB299416
Gene Name; adiponectin receptor 2
Gene Symbol; Adipor2
Genomic Location; chr6: 119, 302, 000-119, 370, 000
Synonyms; D6Uclale
NCBI Gene ID; 68465
MGI ID; 93830
IGTC ID; 287
KEGG Pathway; mmu04920 Adipocytokine signaling pathway
CARD ID; 1437

To begin with, this Ayu21-B196 ES cell was used in an attempt to produce a chimeric mouse according to a general method. ICR female mice plugged by mating with male mice after ovarian hyperstimulation were purchased to collect 2-cell stage embryos by oviduct perfusion. A KSOM medium was used to culture overnight and normal embryos that have developed to 4-cell stage embryos or morula stage embryos were used to produce chimeric mice by an aggregation technique.

Following removal of zona pellucida from the normal embryo, several tens of Ayu21-B196 ES cells per embryo were sprinkled on the embryos for aggregation and the resultant was cultured overnight. The 145 fused embryos were transferred into five surrogate mothers (pseudopregnant ICR female mice). After 17 days, C-section was performed but all of the embryos died during the development and no live chimeric mouse was obtained.

Hence, we tried to produce a chimeric mouse according the method of the present invention. Similar to the general method, ICR female mice plugged by mating with male mice after ovarian hyperstimulation were purchased to collect 2-cell stage embryos by oviduct perfusion. A KSOM medium was used to culture overnight and normal embryos that have developed to 4-cell stage embryos or manila stage embryos were used to produce chimeric mice by an aggregation technique.

Ayu21-B196 ES cell was mixed with a helper ES cell (Ayu21-16EG4 ES cell strain) and sprinkled on the normal zona-free embryos for aggregation and the resultant was cultured overnight. The 125 fused embryos were transferred into five surrogate mothers.

After 17 days, three surrogate mothers had natural births for a total of 10 pups, among which, eight had black eyes and two had white eyes. C-section was performed on the remaining two surrogate mothers but there was no live pup. Three 100% chimeric male mice as judged from the fur colors were obtained and they were mated with B6 female mice. Genotype of their pups (F1) were examined and confirmed that mice with reporter gene geo, namely Ayu21-B196 ES cell-derived mice, were present. Specifically, Ayu21-B196 ES cell that didn't even result in a chimeric mouse according to a general method gave 100% chimeric mice by using a helper ES cell and was confirmed to be incorporated into the germline.

With respect to the ten ES cell strains which were unable to establish a mouse line by themselves, six mouse lines were established by using the method of the present invention.

A number of genes that play important role in spermatogenesis such as Ar (androgen receptor), Kit (kit oncogene) and Texll (testis expressed gene 11) have been reported. The database MGI (Mouse Genome Informatics) hosted by the Jackson Laboratory provides database of Mammalian Phenotype Ontology Annotations that includes various mouse phenotypes. This database shows mouse lines (200 strains) with phenotypes associated with "arrest of spermatogenesis" (failure of spermatogenesis). This list is easily accessible and available from the website on the WorldWideWeb at informatics.jax.org/javawi2/servlet/
WIFetch?page=mpAnnotSummary&id=MP:0001155.

From now, such ES cells in which genes important to spermatogenesis have been knocked out can be utilized as helper ES cells to further improve the results.

Example 2

In the same manner as Example 1, an ES cell strain that could not give a chimeric mouse with a high chimerism rate and thus could not establish a strain according to a general method was mixed with CTB28 ES cell strain (helper ES cell, NITE ABP-1136) to produce a chimeric mouse. Furthermore, a male chimeric mouse was mated with a normal female mouse to see whether sperm derived from the ES cell of interest fertilized to deliver a pup, in other words, whether the ES cell of interest was incorporated into the gem dine in the chimeric mouse. The results are shown in Table 2.

Three different ES cell strains were subjected to the experiment and F1 mice derived from the ES cell of interest were obtained for all strains (100%) (Table 2).

TABLE 2

| | | State of germline | |
|---|---|---|---|
| No. | Name of ES cells | Single line | Ayu21-16EG4-mixed line |
| 1 | Ayu21-W52 | x | o |
| 2 | Ayu21-W234 | x | o |
| 3 | Ayu21-W321 | x | o |

INDUSTRIAL APPLICABILITY

A method of the present invention is advantageous in that a mouse strain can efficiently be established from a pluripotent stem cell.

The invention claimed is:
1. A method for producing a chimeric mouse, the method comprising the step of transferring an aggregate of a first pluripotent stem cell, a second pluripotent stem cell comprising an epigenetic modification associated with lack of or low ability to form germ cells, and an embryo into a host mouse, wherein the first pluripotent stem cell is incorporated into the germline of the embryo for the purpose of strain establishment, wherein the second pluripotent stem cell is a cell deposited with the Patent Microorganisms Depositary, National

Institute of Technology and Evaluation (Japan), and identified by accession number NITE BP-973, accession number NITE BP-1135, or accession number NITE BP-1136, and wherein the host mouse is a prepared pseudopregnant mouse and the embryo in the aggregate is a chimeric embryo, and wherein, upon transfer to the uterus of the host mouse, the host mouse carries the embryo to term, thereby producing the chimeric mouse.

2. The method according to claim 1, wherein the pluripotent stem cell is an embryonic stem (ES) cell or an induced pluripotent stem (iPS) cell.

3. The method according to claim 1, wherein the ability to form germ cells is spermatogenetic ability.

4. A helper cell for enhancing strain establishment efficiency of a pluripotent stem cell that is to be incorporated into the germline of an embryo for the purpose of strain establishment, wherein the helper cell is a cell deposited with the Patent Microorganisms Depositary, National Institute of Technology and Evaluation (Japan), and identified by accession number NITE BP-973, NITE BP-1135 or NITE BP-1136.

* * * * *